United States Patent [19]
Kartchner

[11] Patent Number: 5,980,824
[45] Date of Patent: Nov. 9, 1999

[54] RADIO FREQUENCY ANIMAL WASTE TREATMENT APPARATUS

[76] Inventor: Henry H. Kartchner, 15311 Vantage Pkwy. West, Houston, Tex. 77032

[21] Appl. No.: 09/026,134

[22] Filed: Feb. 19, 1998

[51] Int. Cl.$^6$ ............................................. A61L 2/08
[52] U.S. Cl. .................... 422/22; 422/186; 422/209; 422/225; 422/233; 422/241; 422/900; 250/455.11
[58] Field of Search ............... 422/22, 186, 209, 422/224, 225, 232, 233, 240, 241, 900; 250/453.11, 454.11, 455.11

[56] References Cited

U.S. PATENT DOCUMENTS

| | | | |
|---|---|---|---|
| 4,702,808 | 10/1987 | Lemelson | 422/186 |
| 4,883,570 | 11/1989 | Efthimion et al. | 422/186 |
| 4,978,501 | 12/1990 | Diprose et al. | 422/22 |
| 5,134,946 | 8/1992 | Poovey | 422/186 |
| 5,326,530 | 7/1994 | Bridges | 422/22 |
| 5,523,052 | 6/1996 | Bridges e tal. | 422/22 |
| 5,609,820 | 3/1997 | Bridges et al. | 422/22 |
| 5,641,423 | 6/1997 | Bridges et al. | 422/22 |
| 5,655,210 | 8/1997 | Gregoire et al. | 422/186 |
| 5,784,682 | 7/1998 | Birken et al. | 422/186 |
| 5,833,922 | 11/1998 | Held et al. | 422/22 |

*Primary Examiner*—Robert J. Warden, Sr.
*Assistant Examiner*—Fariborz Moazzam
*Attorney, Agent, or Firm*—Ezra L. Schacht

[57] ABSTRACT

A microwave applicator chamber to effectively sterilize animal waste having a series of rotating chamber sectors carrying the waste under a source of intense radio frequency energy. The animal waste emerges free of pathogens and odor causing bacteria, ready for incorporation into plant fertilizers.

6 Claims, 3 Drawing Sheets

RADIO FREQUENCY ANIMAL WASTE TREATMENT APPARATUS

BACKGROUND OF THE INVENTION

The ample production of beef, pork, chicken and dairy products in large scale, centralized animal production facilities to meet the growing demand for a high protein diet in our wealthy society have been accomplished with increasing economy. High quality meat and milk products are delivered to the grocer's shelves at bargain prices. Unfortunately, the byproduct of centralized animal husbandry are ever growing open pits or lagoons of untreated, semi-liquid animal wastes.

Recent concerns over the possibility of pathogens in these animal wastes leaking into lakes and rivers or entering the underground water supply have provoked civic actions. intestinal parasites, such as giardia and cryptosporidium and pathogenic viruses and bacteria, which can infect man, are capable of entering the watershed from theme animal waste ponds. If these plant nutrient containing byproducts enter our lakes and rivers, the normal ecology is overwhelmed by "blooms" of algae which use up all the dissolved oxygen, killing fish and other aquatic creatures. These animal manures, if properly treated and applied, become useful plant fertilizers and complete the nutrient cycle if returned to the land for crop production.

The present invention proposes to treat animal wastes with intense radio frequency energy to destroy all pathogens. Semi-liquid manures are pumped into a specialized multimode, resonant chamber with a series of moving partitions, each of which moves animal waste products in sectors into the path of the radio frequency energy for sterilization.

For portable, on-site treatment of existing animal waste lagoons, all necessary equipment is brought to the site and operated from a trailer mounted, self contained system. The complete system has a portable electricity generator, a portable radio frequency energy generator, semi-liquid animal waste handling pumps with flexible piping, the [RF] radio frequency energy applicator assembly and treated animal waste retaining and bagging equipment. Stationary and permanent installations can be added to the final stage, waste treatment procedures at existing dairies, farms and feedlots.

Exiting treated wastes can be mixed with moisture adsorbing materials and fortified with additional nutrients and trace minerals to produce rich fertilizer pellets. the pellets can be bagged for storage or shipped for immediate use.

Description of the Prior Art

Kishi (U.S. Pat. No. 5,152,074) proposes a drying apparatus having a casing provided with stirring blades and heating bodies therein (col. 1 lines 65–68) in which the raw sewage is stirred by the rotation of the stirring blades and heated by the heat generated by the heating bodies.

There are significant differences between Kishi and applicant. Although Kishi lists several continuing applications, those available to applicant at this writing all seem to be based upon the use of microwave or magnetic flux to heat ceramic or metallic balls 29, and to completely dry the raw sewage to a sterile ash for ease of disposal. Kishi describes a portable toilet. He claims a raw sewage drying apparatus comprising a casing, a rotating drive shaft unit having a plurality of blades for stirring the raw sewage, and bodies or ball elements capable of being heated by directing electromagnetic waves toward the casing. The ball elements are made from a radio frequency energy adsorbing material and transfer enough heat to the surrounding sewage to dry and pulverize to a powdery ash for vacuum collection in a dust collector. In applicant's invention the need for ball elements are unnecessary. The radio frequency energy heats the waste directly, because of the high dielectric absorption of the water contained within the waste. Applicant's rotating partition walls simply move accumulated waste in sectors under the radio frequency energy window for exposure to intense radio frequency energy.

The objectives of applicant are to directly heat the pathogens in the manure and to prepare a material to serve as a base for a fertilizer.

Simon (U.S. Pat. No. 3,997,388) claims a method and apparatus to dry manure with microwave radiation at the preferred frequency of 2450 Maz in combination with ultrasonic energy to accelerate evaporation and discourage matter from adhering to the surfaces.

Applicant relies upon slick vertical, polymer surfaces and wiping action to discourage adhesion of semi-liquid wastes. The ultrasonic energy introduced by Simon is unnecessary in the applicant's invention.

DETAILED DESCRIPTION OF THE DRAWINGS

Figure 1:
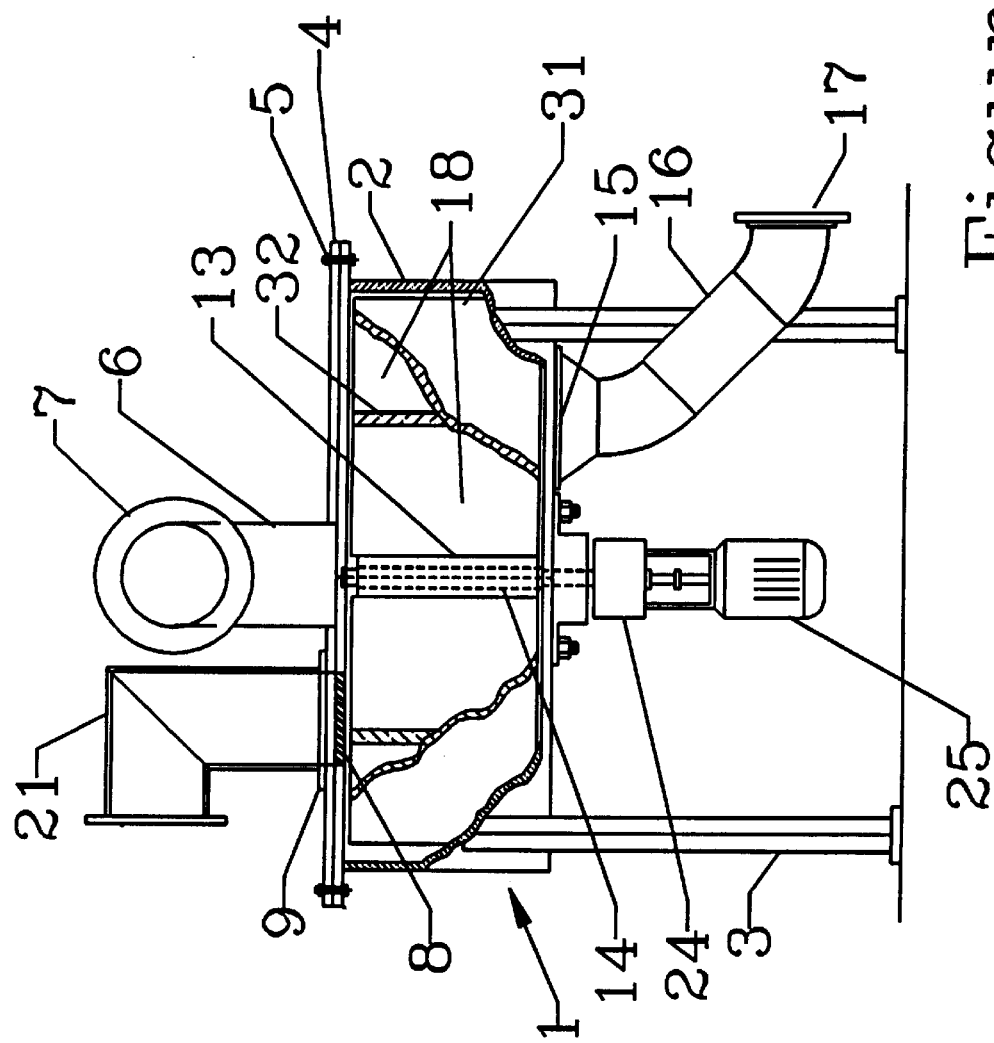
FIG. 1 is an elevated view of a radio frequency energy waste treatment chamber.
Figure 2:
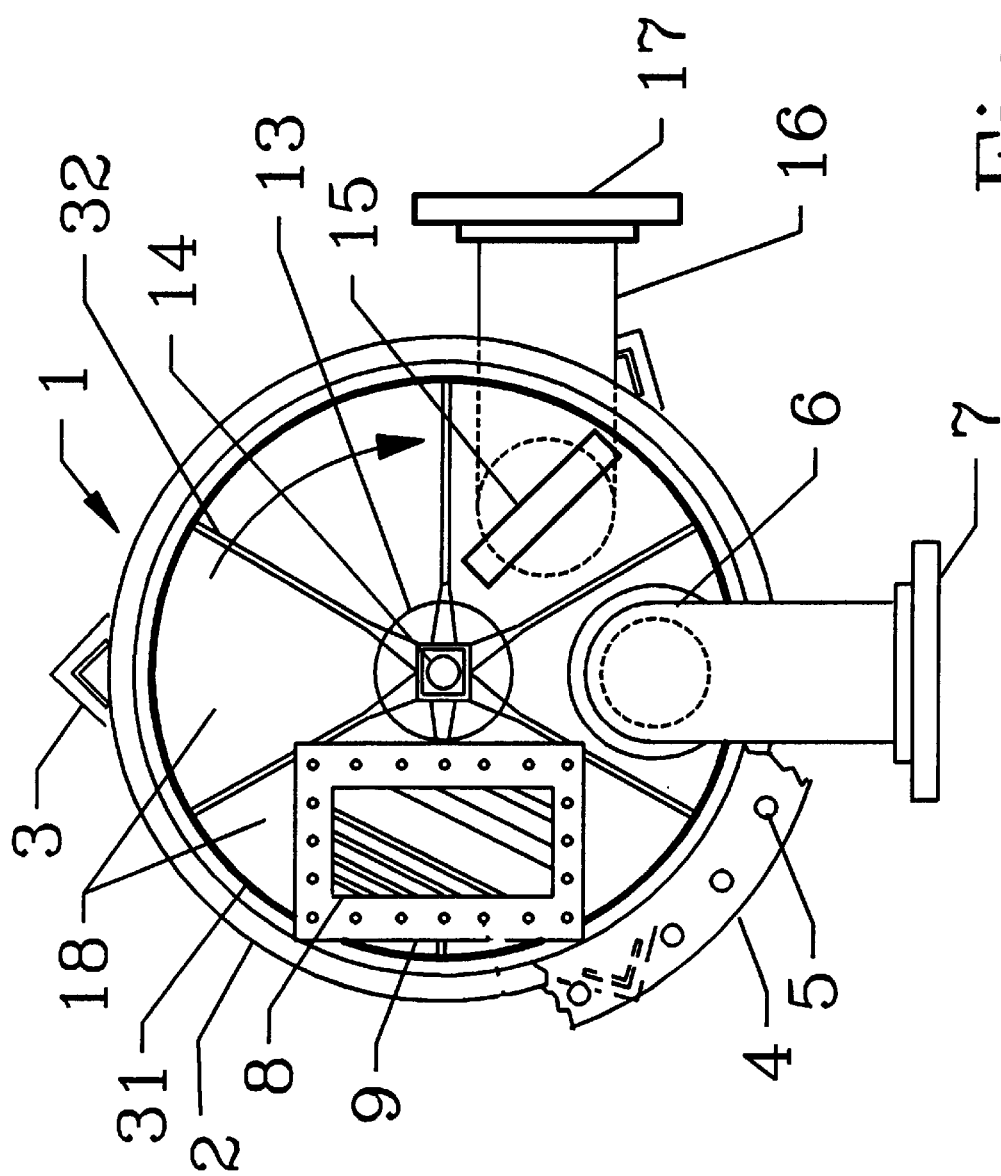
FIG. 2 is a plan view of the radio frequency energy waste treatment chamber.

A radio frequency (RF) energy treatment chamber 1, as detailed in the elevated view of FIG. 1 and plan view FIG. 2, has an animal waste inlet pipe 6 with flange 7 and a treated waste outlet pipe 16 with flange 17. High power radio frequency energy is admitted by means of waveguide 21 and through radio frequency transparent window 8 made of thick TEFLON® or other chemically inert, high temperature material. Chemically inert and radio frequency transparent drum assembly 31 having radio frequency transparent partitions 32 radiating in a spoke like pattern form a central cylindrical hub 13 are driven in a rotating fashion by driveshaft 14 attached to motor 25 through geared speed reducer 24. Motor 25 and geared speed reducer 24 can be mounted on the top of treatment chamber 2 for ease of access and protection from water. Untreated waste entering through inlet pipe 6 fills the sectors 18 between partitions 32 and is carried by the rotation of the drum assembly passed the transparent window 8 where the waste absorbs enough radio frequency energy for sterilization to occur.

Each sector 18 is open at the top and bottom or the drum assembly. The drum assembly is contained within the metal walled outer chamber 2 with metal lid 4 held in place with fasteners 5. The radio frequency energy in totally contained within this chamber. The metal chamber 2 is shown with supports 3. Treated waste sterilization in controlled by the retention time of the wastes within the radio frequency energy zone. The radio frequency energy input power demand and drive motor speed in controlled by monitoring treated waste outlet temperature. The benign, treated waste exit slot 15 acts to empty the chamber of waste by a combination of gravity and the wiping motion of the lower edge of partitions 32. The non-adhesiveness of TEFLON® and other inert fluorocarbon polymers used for the partitions and the drum walls prevents the adherence of the waste to the surfaces. Vents not shown) allow for the exit of water vapor and team from the treated semi-liquid waste stream. An exit valve mechanism (not shown) can control the rate of treated waste egress from the chamber.

Figure 3:
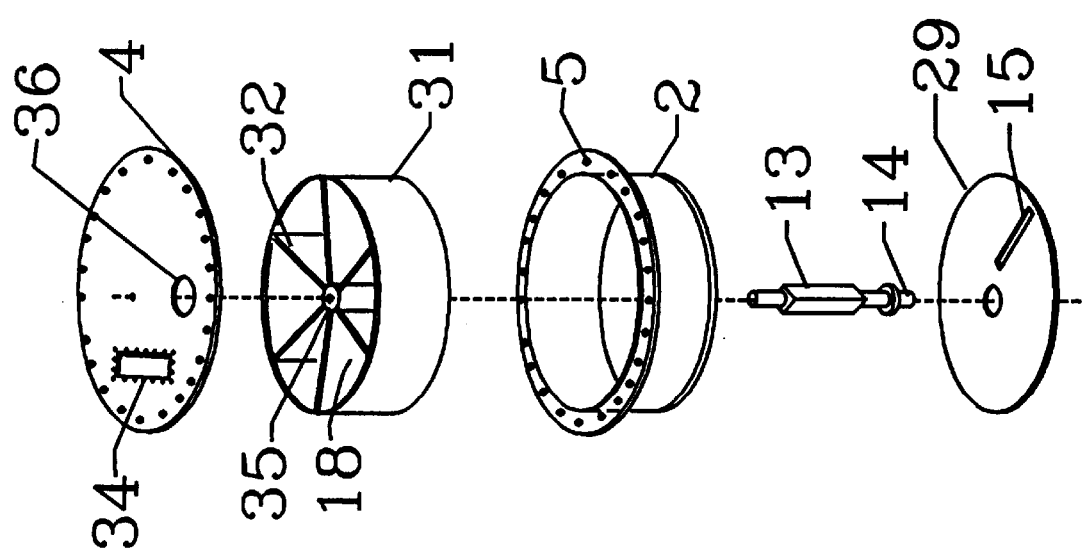
FIG. 3 shows an exploded isometric view of key elements of the treatment chamber.

FIG. 3 details an exploded view of one embodiment of the invention. Outer metal chamber 2 with top flange 4 and mounting holes 5 has welded bottom plate 29 (shown disconnected) with opening to admit drive shaft 14 and treated waste exit slot 15. Exit slot 15 is dimensioned or screened to prevent radio frequency energy loss and still permit the exiting of treated waste.

Drive shaft 14 has square or keyed shaft to engage and drive the hub 13 of radio frequency transparent drum assembly 31. Drum assembly 31 has radio frequency transparent partitions 32 to push the waste along from entrance port 36 to radio frequency energy inlet port 34 which connects to inlet flange 9 as detailed in FIG. 1.

Hub 35 can be constructed of radio frequency reflective metal and of suitable dimensions to act in conjunction with outer chamber wall 2, bottom plate 29 and top cover 4, as a multi-mode, multi-path, resonant chamber for radio frequency energy. The use of TEFLON® or other high temperature inert and radio frequency energy transparent material for construction of partitions 32 allow the radio frequent energy to reach adjacent waste sectors. Waste within the contained volume will be swept past several regions of maximum radio frequency energy to guarantee proper heating and sterilization.

Radio frequency energy is applied by commercially available power oscillators with outputs in the 10 kilowatt to 100 kilowatt or higher range. Approved industrial frequencies of 925 MHz and 2450 MHz can be used. At these frequencies water contained in the wastes readily absorbs the radio frequency energy.

The apparatus and methods described in applicant's invention are not limited to animal wastes. Other organic waste products such as human fecal wastes and slaughterhouse offal that need sterilization to prevent the growth of pathogens and parasites, and to limit the malodorous byproducts of bacterial fermentation can be treated by the means herein described.

Applicant's invention can be used to sterilize food and beverage ingredients prior to processing. In particular, in the preparation of alcoholic beverages or bakery products, where sterile ingredients are needed prior to inoculation with yeast.

What is claimed is:

1. An apparatus for the treatment of semi-liquid feedstocks comprising;
   a metal walled chamber having a top, bottom and cylindrical sides;
   a source of radio frequency energy,
   a sectored, radio frequency transparent, partitioned drum assembly driven by rotating means and contained within said metal walled chamber;
   an inlet port in said metal walled chamber for the introduction of the semi-liquid feedstocks;
   an outlet port in said metal walled chamber for the egress of said semi-liquid feedstocks;
   and, a radio frequency energy inlet window in said metal walled chamber;
   forming a multi-mode radio frequency resonant chamber for said radio frequency energy to render said semi-liquid feedstocks free of pathogens.

2. An apparatus as described in claim 1, in which said semi-liquid feedstocks are comprised of animal wastes.

3. An apparatus as described in claim 1, in which said semi-liquid feedstocks are comprised of human wastes.

4. An apparatus as described in claim 1, in which said semi-liquid feedstocks are comprised of vegetable byproducts.

5. An apparatus as described in claim 1, in which said semi-liquid feedstocks are comprised of food products in need of sterilization prior to further processing.

6. A method of treatment of semi-liquid feedstocks, the steps comprising;
   introducing said semi-liquid feedstocks into a metal walled, multi-mode, radio frequency resonant chamber having a top, bottom and cylindrical sides, through a feedstock inlet port and into a sectored, radio frequency transparent, partitioned drum assembly driven by rotating means and contained within said metal walled chamber;
   exposing said semi-liquid feedstock to radio frequency energy through a radio frequency energy transparent inlet window in said metal walled chamber;
   rendering said semi-liquid feedstocks free of pathogens with said radio frequency energy; and
   discharging said pathogen free semi-liquid feedstock from an outlet port in said metal walled chamber.

* * * * *